(12) United States Patent
Uenohara et al.

(10) Patent No.: US 8,382,790 B2
(45) Date of Patent: Feb. 26, 2013

(54) MANIPULATOR

(75) Inventors: Shuichi Uenohara, Fujinomiya (JP); Hiroaki Sano, Fujinomiya (JP)

(73) Assignee: Terumo Kabushiki Kaisha, Tokyo (JP)

( * ) Notice: Subject to any disclaimer, the term of this patent is extended or adjusted under 35 U.S.C. 154(b) by 251 days.

(21) Appl. No.: 12/391,506

(22) Filed: Feb. 24, 2009

(65) Prior Publication Data

US 2009/0216248 A1    Aug. 27, 2009

(30) Foreign Application Priority Data

Feb. 26, 2008  (JP) ................................. 2008-045076
Jan. 29, 2009  (JP) ................................. 2009-017796

(51) Int. Cl.
*A61B 17/00* (2006.01)

(52) U.S. Cl. ............................. 606/205; 606/51; 606/52

(58) Field of Classification Search .......... 606/205–208, 606/51, 52, 167–170
See application file for complete search history.

(56) References Cited

U.S. PATENT DOCUMENTS

| | | | |
|---|---|---|---|
| 4,294,233 A | | 10/1981 | Takahashi |
| 4,545,369 A | * | 10/1985 | Sato ............... 600/133 |
| 4,646,751 A | * | 3/1987 | Maslanka ............ 600/564 |
| 5,035,248 A | * | 7/1991 | Zinnecker ............ 600/564 |
| 5,395,364 A | * | 3/1995 | Anderhub et al. ........... 606/51 |
| 5,454,825 A | | 10/1995 | Van Leeuwen et al. |
| 5,620,459 A | | 4/1997 | Lichtman |
| 5,810,876 A | * | 9/1998 | Kelleher ............... 606/205 |
| 6,331,181 B1 | | 12/2001 | Tierney et al. |
| 6,994,716 B2 | | 2/2006 | Jinno et al. |
| 2004/0266574 A1 | | 12/2004 | Jinno et al. |
| 2005/0261735 A1 | * | 11/2005 | Shibata ............... 606/205 |
| 2006/0058825 A1 | | 3/2006 | Ogura et al. |
| 2008/0188890 A1 | * | 8/2008 | Weitzner et al. ........... 606/205 |
| 2008/0242925 A1 | * | 10/2008 | Suda ............... 600/104 |

FOREIGN PATENT DOCUMENTS

| | | |
|---|---|---|
| EP | 0 647 433 A1 | 4/1995 |
| EP | 1 462 147 A1 | 9/2004 |
| EP | 1 693 018 A1 | 8/2006 |
| JP | 2004-105451 | 4/2004 |

OTHER PUBLICATIONS

European Search Report issued Mar. 23, 2012 in European Patent Application No. 12150235.5.
European Search Report issued Mar. 23, 2012 in European Patent Application No. 12150234.8.

* cited by examiner

*Primary Examiner* — Gary Jackson
*Assistant Examiner* — Katrina Stransky
(74) *Attorney, Agent, or Firm* — Oblon, Spivak, McClelland, Maier & Neustadt, L.L.P.

(57) ABSTRACT

A manipulator includes a hollow joint shaft, wires extending through the joint shaft, pulleys mounted on an end of the joint shaft, for imparting a drive force to the wires, a distal-end working unit mounted on another end of the joint shaft, for being actuated by the wires, and a sealing member for preventing liquid such as blood from flowing from the distal-end working unit through the joint shaft to a connector. The sealing member has holes defined therein, and the wires are slidably inserted through the holes.

14 Claims, 15 Drawing Sheets

MANIPULATOR

BACKGROUND OF THE INVENTION

1. Field of the Invention

The present invention relates to a manipulator for operating a distal-end working unit through power transmitting members.

2. Description of the Related Art

According to endoscopic surgery (also called laparoscopic surgery), it is customary to form a plurality of holes or incisions in the body surface (abdomen or the like) of the patient, insert trocars (tubular instruments) into the respective incisions as instrument passage ports, and introduce tip ends of forceps having shafts through the respective trocars into the body cavity to perform the surgical operation on the affected part of the body. Working units such as a gripper for gripping a living tissue, scissors, the blade of an electrosurgical knife, etc. are mounted on the tip ends of the forceps.

The endoscopic surgical operation performed with forceps requires the surgeon to be trained in advance because the working space in the body cavity is small and the forceps need to be operated using the trocars as fulcrums. Since the forceps that have been used heretofore have no joints in the working unit on the tip end thereof, the forceps have a small degree of freedom and the distal-end working unit of the forceps can be operated only on an extension of the shaft. Therefore, cases that can be handled under the usual training practice for endoscopic surgery are limited to a certain range, and the surgeon need to be trained and skilled to a considerably high level in order to be able to perform endoscopic surgery on various other cases not in the limited range.

Attempts have heretofore been made to improve conventional forceps and develop forceps having a plurality of joints in a working unit thereof (see, for example, Japanese Laid-Open Patent Publication No. 2004-105451). The developed forceps, which may also be referred to as a manipulator, is free of the limitation and difficulties of the conventional forceps, can be operated with easy techniques, and can be applied to a wide variety of cases.

The manipulator comprises a working unit having a distal-end working unit (also referred to as an end effector) mounted on the distal end of a slender shaft. The main body (operating unit) has actuators for actuating the distal-end working unit through wires. The wires are wound around respective pulleys in the proximal end portion of the working unit.

There has been proposed a medical robot system including such manipulators movable by robot arms (see U.S. Pat. No. 6,331,181, for example). The medical robot system can be remotely controlled by an operating unit which comprises a joy stick and a master arm and can be operated in various patterns under programmed control. The medical robot system has a plurality of robot arms that are selectively used to perform respective surgical techniques. One of the robot arms supports an endoscope for capturing an image in a body cavity which is to be confirmed on a display monitor.

The manipulator tends to be smeared with the blood and body fluids of the patient while a surgical technique is being performed on the patient. Therefore, the manipulator needs to be cleaned and sterilized after the surgical technique has been performed.

However, since the distal-end working unit of the manipulator has a plurality of joints, the blood and body fluids of the patient are likely to flow into the manipulator through the joints. As it is tedious and time-consuming to clean the manipulator, it has been desired in the art that the manipulator be of a structure which can easily cleaned and sterilized.

Particularly, the blood and body fluids may possibly find their way from the distal-end working unit deeply into the slender shaft through which the wires extend and also occasionally into the main body of the manipulator. If the blood and body fluids have entered the slender shaft and the main body, then it is more tedious and time-consuming to clean the manipulator.

SUMMARY OF THE INVENTION

It is an object of the present invention to provide a manipulator which prevents blood or the like from flowing into the shaft to a maximum extent and which can be cleaned with ease.

According to an aspect of the present invention, there is provided a manipulator comprising a hollow shaft, a power transmitting member extending through the hollow shaft, a drive mechanism mounted on one end of the hollow shaft, for imparting a drive force to the power transmitting member, a distal-end working unit mounted on another end of the hollow shaft, for being actuated by the power transmitting member, and a sealing member for preventing liquid from flowing from the distal-end working unit through the hollow shaft to the drive mechanism, the sealing member having a hole defined therein, the power transmitting member being slidably inserted through the hole.

The sealing member is capable of blocking the liquid tending to flow from the distal-end working unit through the hollow shaft to the drive mechanism. Therefore, the liquid is prevented from being introduced deeply into the hollow shaft and the drive mechanism. The manipulator can thus be cleaned easily after use, and hence can easily be serviced for maintenance. Also, since the sealing member is capable of blocking air flow in the shaft, air is substantially sealed in the interior of the shaft on the distal end working unit side of the sealing member. Thus, the sealed air can prevent blood or the like from flowing into the shaft, to a maximum extent.

The sealing member may be disposed in the hollow shaft and divide the interior of the hollow shaft into a compartment near the distal-end working unit and a compartment near the drive mechanism, so that the liquid is prevented more reliably from flowing from the distal-end working unit through the hollow shaft to the drive mechanism.

The power transmitting member may have at least a first portion which is flexible and a second portion which is more rigid than the first portion, the second portion extending through the hole. With this arrangement, any gaps occurring between the inner wall surface of the hole and the power transmitting member are minimized, allowing the sealing member to have a better sealing capability.

Preferably, when the power transmitting member is operated, the second portion is slidably held in the hole at all times.

The second portion may comprise a reinforcing tube surrounding a portion of the first portion or a bar member coupled to the first portion.

The manipulator may further comprise a cleaning tube extending from the drive mechanism side toward the distal-end working unit side, for supplying a cleaning solution therethrough for cleaning the interior of the distal-end working unit. The sealing member may have a cleaning hole defined therein, the cleaning tube extending through the cleaning hole, and the cleaning tube may have an end facing the distal-end working unit and disposed more closely to the distal-end working unit than the sealing member. The cleaning tube thus positioned is effective to clean the hollow shaft and the distal-end working unit easily with the cleaning solution.

The manipulator may further comprise a plug removably mounted on an end of the cleaning tube near the drive mechanism. Alternatively, the manipulator may further comprise a check valve connected to a portion of the cleaning tube which is closer to the drive mechanism than the sealing member, for preventing the cleaning solution from flowing from the distal-end working unit toward the drive mechanism. Since the plug or the check valve can keep the internal pressure in the hollow shaft at a certain level while the manipulator is in use, liquid such as blood is effectively prevented from flowing into the cleaning tube from the open distal end of the cleaning tube.

Further, the sealing member may have a slit extending from an outer surface thereof to the hole. In this case, the power transmitting member is firstly looped, and then the looped power transmitting member is inserted into the hole through the slit. Thus, the manipulator can be assembled more easily.

Also, according to another aspect of the present invention, a manipulator comprises a hollow shaft, a power transmitting member extending through the hollow shaft, a drive mechanism mounted on one end of the hollow shaft, for imparting a drive force to the power transmitting member, a distal-end working unit mounted on another end of the hollow shaft, for being actuated by the power transmitting member, and a sealing member for preventing liquid from flowing from the distal-end working unit through the hollow shaft to the drive mechanism, the sealing member having a hole defined therein, the power transmitting member being inserted through the hole, and an elastic member disposed in the hole and fixedly mounted on an outer circumferential surface of the power transmitting member.

With this arrangement, when the power transmitting member is moved, the elastic member fixedly mounted on the outer circumferential surface elastically expands or contracts, whereby flow of liquid such as blood is blocked. Thus, since the sealing member has no contact portion which slidingly contacts with the power transmitting member, force required to move the power transmitting member can be reduced.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Manipulators according to embodiments of the present invention will be described below with reference to the accompanying drawings.

Figure 1:
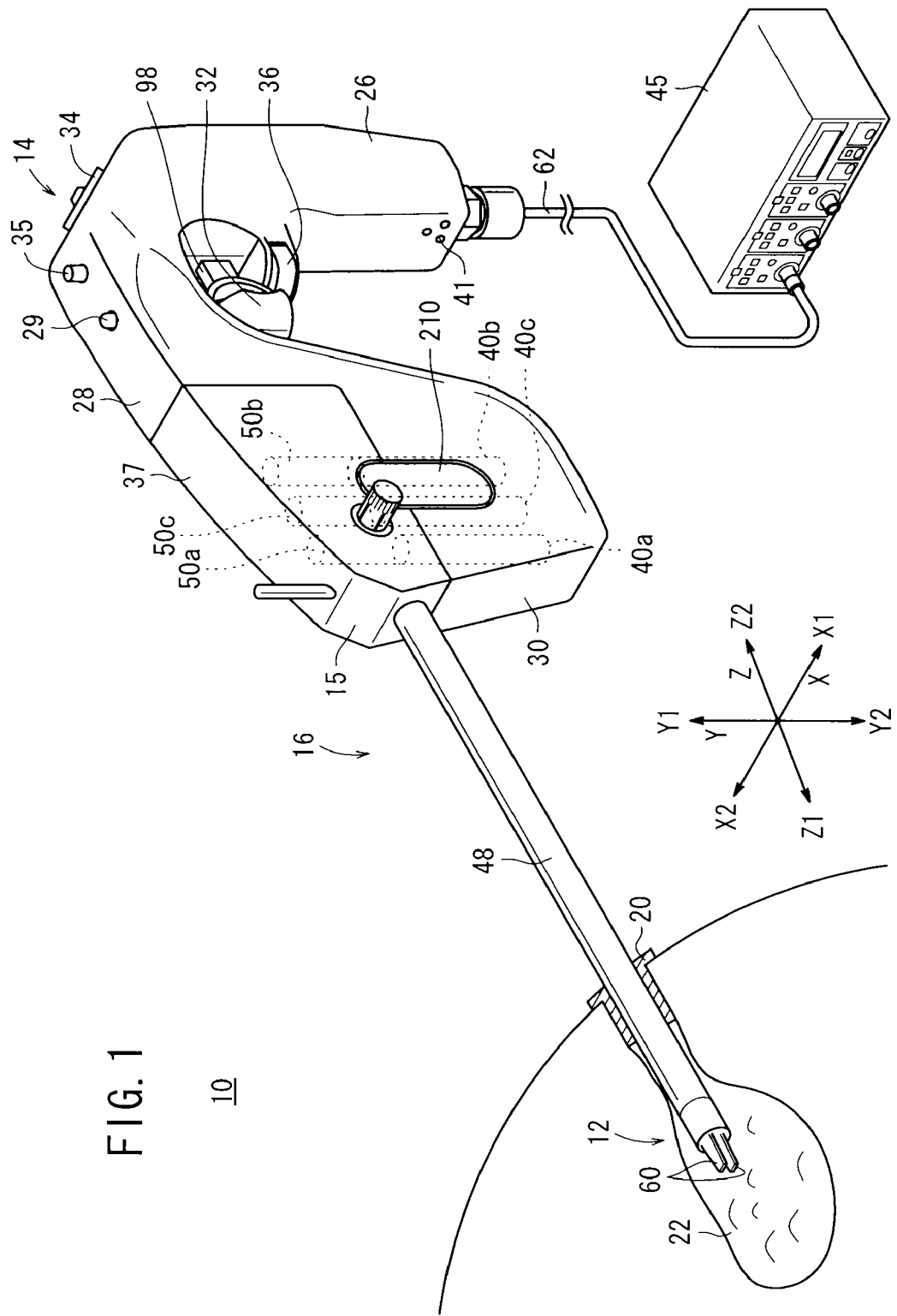
FIG. 1 is a perspective view of a manipulator according to an embodiment of the present invention.

As shown in FIG. 1, a manipulator 10 according to an embodiment of the present invention is a medical manipulator having a distal-end working unit 12 for gripping a portion of a living tissue, a curved needle, or the like for performing a certain surgical treatment, and is usually referred to as gripping forceps or a needle driver (needle holder).

The manipulator 10 comprises an operation command unit 14 which is held and operated by hand and a working unit 16 detachably mounted on the operation command unit 14.

It is assumed in the following description that transverse directions in FIG. 1 are referred to as X directions, vertical directions as Y directions, and longitudinal directions of a joint shaft 48 as Z directions. Of the X directions, the rightward direction as viewed from the distal end is referred to as an X1 direction, and the leftward direction as an X2 direction. Of the Y directions, the upward direction is referred to as a Y1 direction, and the downward direction as a Y2 direction. Of the Z directions, the forward direction is referred to as a Z1 direction, and the rearward direction as a Z2 direction. Unless otherwise noted, these directions represent directions of the manipulator 10 when it is of a standard attitude (neutral attitude). The definition of the above directions is for illustrative purpose only, and the manipulator 10 can be used in any orientations, e.g., it may be used upside down.

The working unit 16 comprises a distal-end working unit 12 for performing working operation, a connector (drive mechanism) 15 connected to an actuator block (actuator, drive mechanism) 30 of the operation command unit 14, and an elongate hollow joint shaft 48 coupling the distal-end working unit 12 and the connector 15 to each other. When a predetermined action is performed on the actuator block 30, the working unit 16 can be separated from the operation command unit 14, so that the working unit 16 can be cleaned, sterilized, and serviced for maintenance.

The distal-end working unit 12 and the joint shaft 48, which are small in diameter, can be inserted into a body cavity 22 through a trocar 20 in the form of a hollow cylinder mounted in an abdominal region or the like of the patient. The distal-end working unit 12 is actuated by the operation command unit 14 to perform various surgical techniques to remove, grip, suture, or tie-knot (ligate) an affected part of the patient's body in the body cavity 22.

The operation command unit 14, which comprises a casing, includes a grip handle 26 gripped by hand, a bridge 28 extending from an upper portion of the grip handle 26, and an actuator block 30 connected to a distal end of the bridge 28.

The grip handle 26 of the operation command unit 14 extends in the Y2 direction from the end of the bridge 28, and has a length suitable for being gripped by hand. The operation command unit 14 includes an input means, disposed near the grip handle 26, for operating the distal-end working unit 12. The input means includes a trigger lever 32 and a switch 36 disposed on the grip handle 26 at the Z1 side, and a composite input unit 34 and an operation switch 35 disposed on the Y1 side of the grip handle 26.

An LED 29 is mounted on the upper surface of the bridge 28 at a location which can easily be viewed by the operator of the manipulator 10. The LED 29 is spaced from the operation switch 35 in the Z1 direction. The grip handle 26 has a plurality of vent holes 41 defined in a lower end thereof. The vent holes 41 function as a pressure regulating mechanism. A cable 62 has an end connected to the lower end of the grip handle 26 and an opposite end connected to a controller 45. The grip handle 26 and the cable 62 may be connected to each other by a connector.

Structural and operational details of the connector 15 and the actuator block 30 will be described below.

Figure 2:
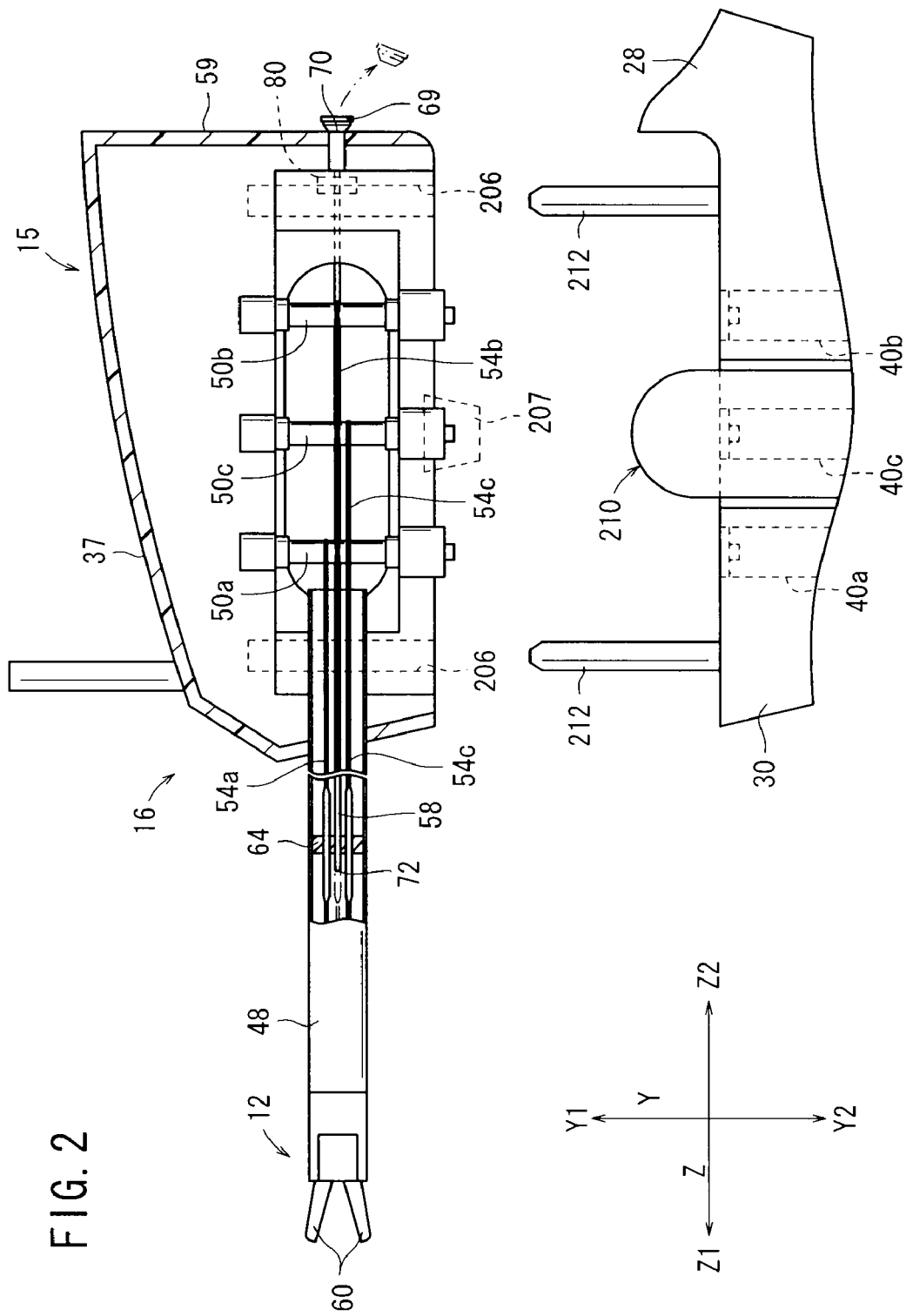
FIG. 2 is a side elevational view of the manipulator with a working unit and an operation command unit being separate from each other.

As shown in FIGS. 1 and 2, the connector 15 is covered with a resin cover 37 and houses pulleys 50*a*, 50*b*, 50*c* rotatably supported therein. Wires 54*a*, 54*b*, 54*c* are wound respectively around the pulleys 50*a*, 50*b*, 50*c* and extend through the hollow joint shaft 48 to the distal-end working unit 12.

Figure 3:
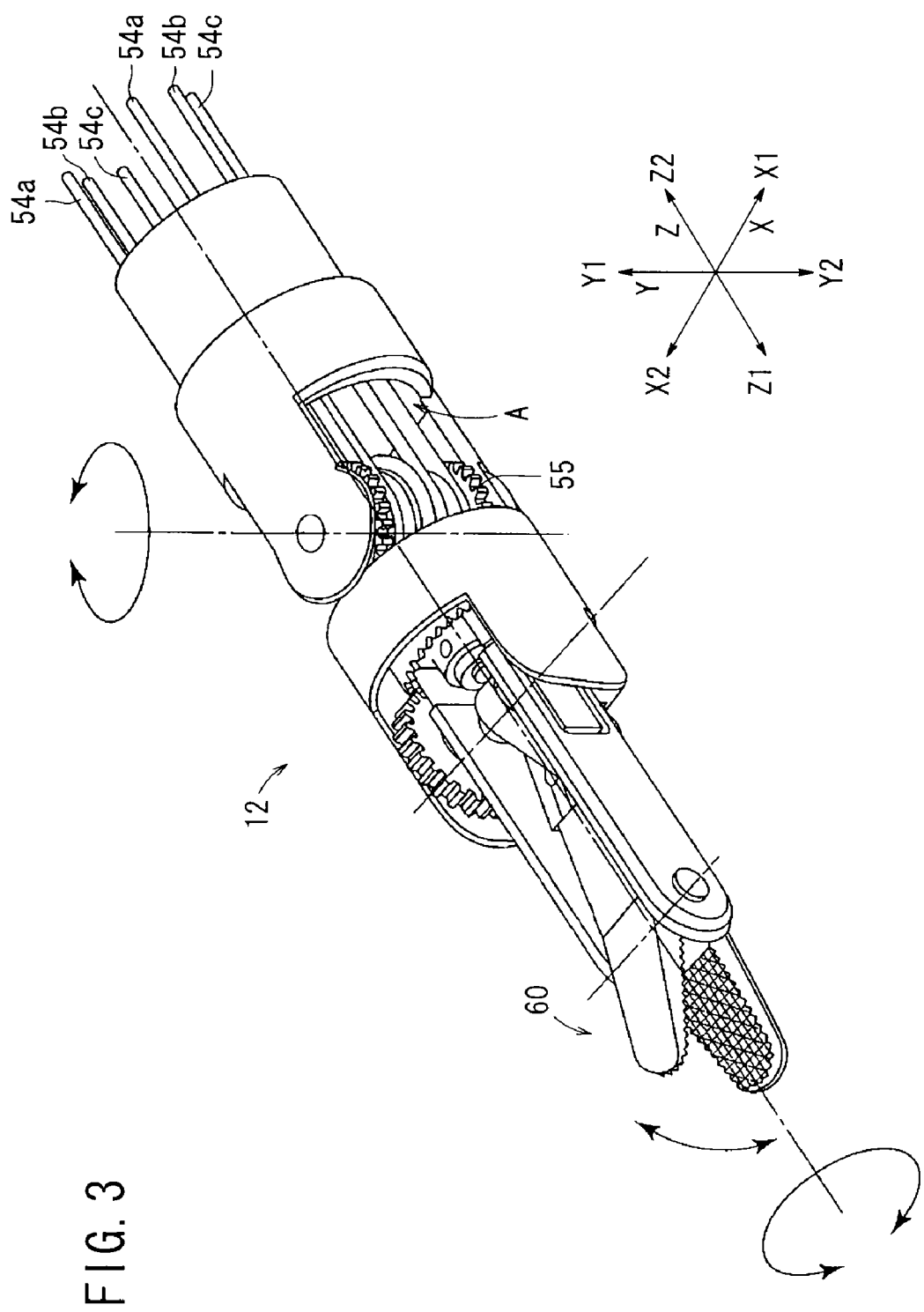
FIG. 3 is a perspective view of a distal-end working unit.

As shown in FIG. 3, the extending wires 54*a*, 54*b*, 54*c* are wound around respective gears 55 in the distal-end working unit 12, which includes a gripper 60. The distal-end working unit 12 has mechanisms of three degrees of freedom for turning the distal-end working unit 12 in rolling directions, i.e., shaft rotating directions, turning the distal-end working unit 12 in yawing directions, i.e., in leftward and rightward directions, and opening and closing the gripper 60.

Figure 4:
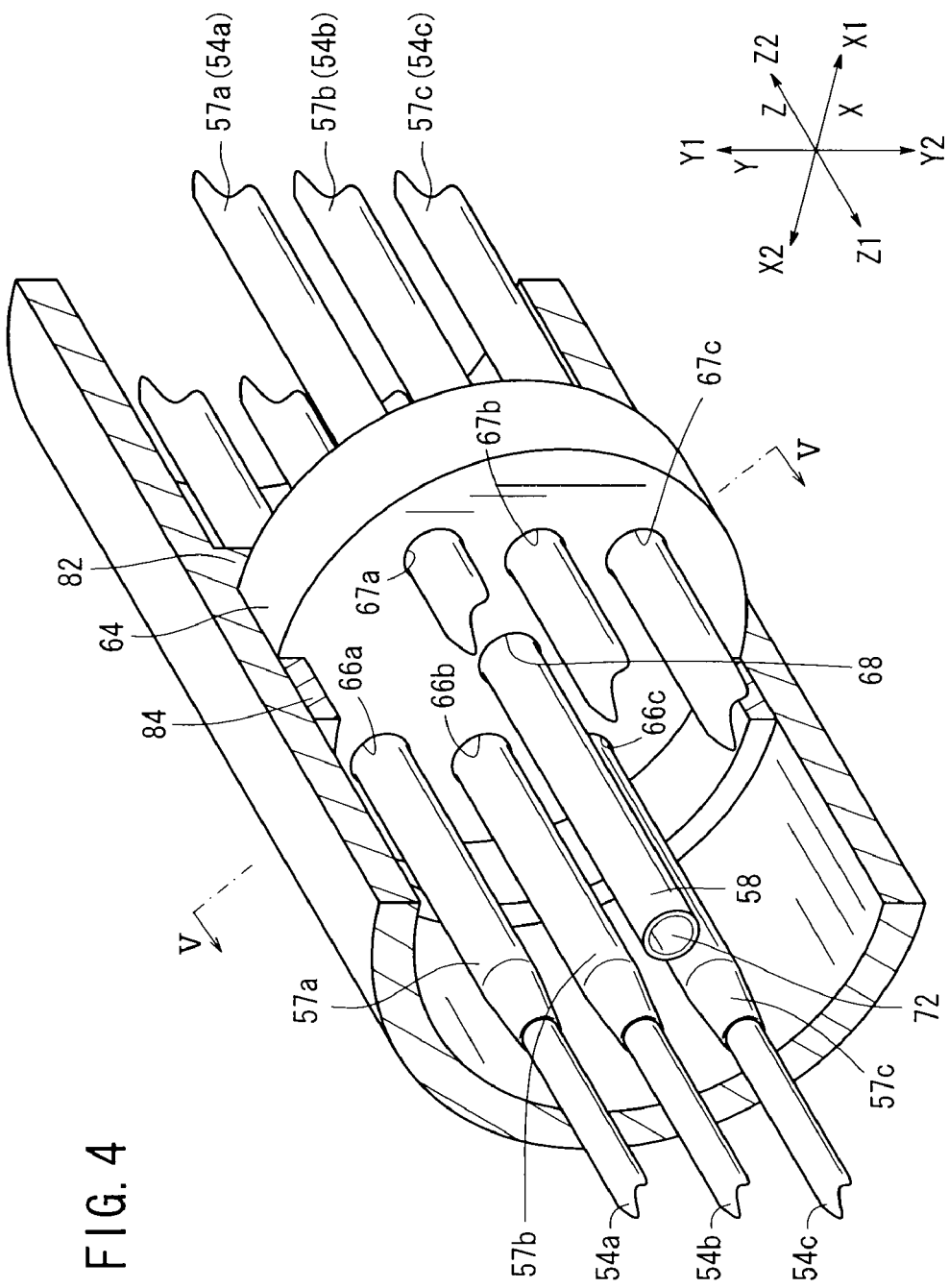
FIG. 4 is a perspective view of a sealing member and nearby parts.

As shown in FIGS. 2 and 4, the wires 54*a*, 54*b*, 54*c* may be of the same type and the same diameter. The wires 54*a*, 54*b*, 54*c* comprise flexible wire material that can be curved. Those straight portions of the wires 54*a*, 54*b*, 54*c* which extend through the joint shaft 48 and which do not need to be flexible are surrounded by and reinforced with reinforcing tubes (hypotubes) 57*a*, 57*b*, 57*c*, respectively. The reinforcing tubes 57*a*, 57*b*, 57*c* are more rigid than the wires 54*a*, 54*b*, 54*c* and so hard that they are not curved in normal use. The reinforcing tubes 57*a*, 57*b*, 57*c* with the wires 54*a*, 54*b*, 54*c* inserted therein have front and rear ends crimped on and securely fixed to the wires 54*a*, 54*b*, 54*c*. The reinforcing tubes 57*a*, 57*b*, 57*c* are made of a biocompatible metal such as stainless steel, for example.

Figure 5:
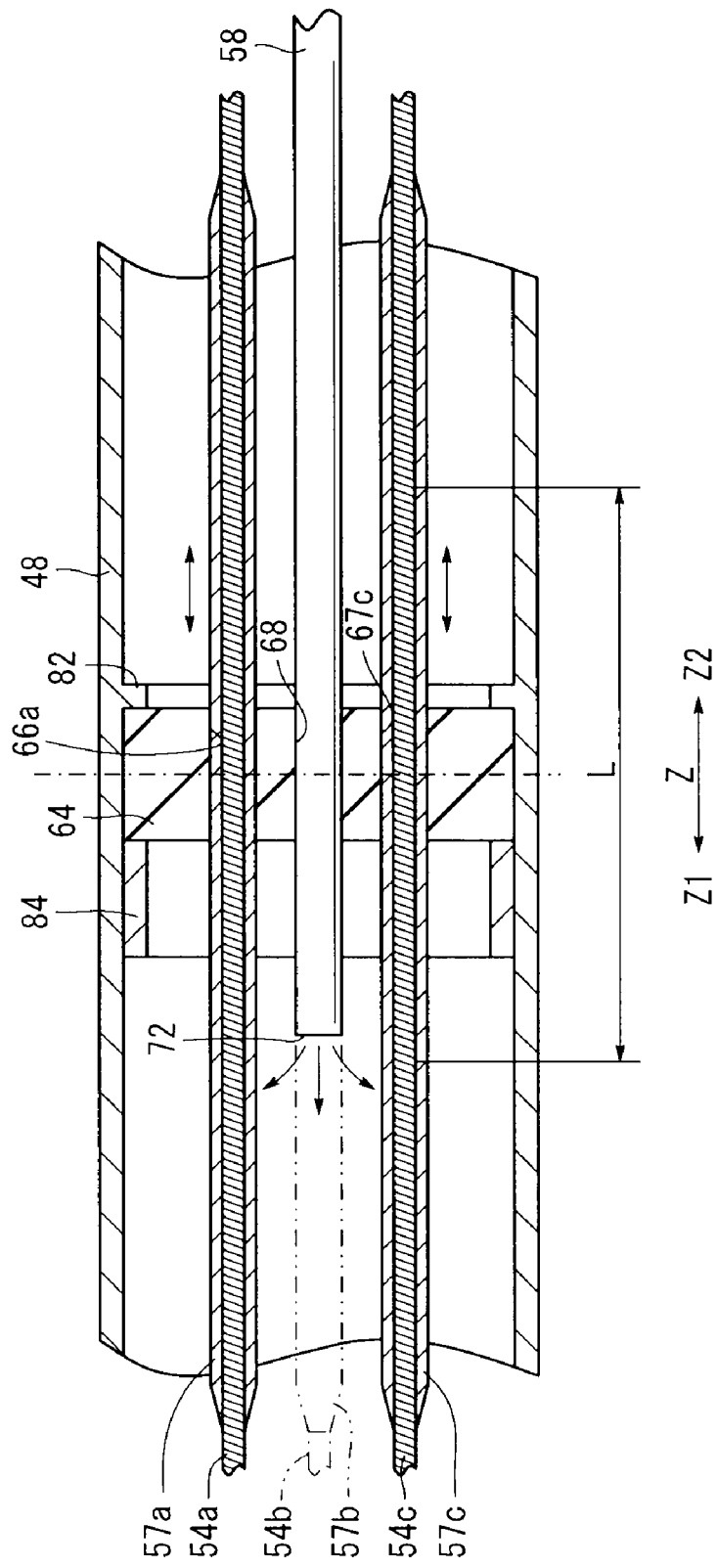
FIG. 5 is a cross-sectional view taken along line V-V of FIG. 4.

The straight portions of the wires 54*a*, 54*b*, 54*c* which are covered with the respective rigid reinforcing tubes 57*a*, 57*b*, 57*c*, i.e., the portions of the wires 54*a*, 54*b*, 54*c* which are disposed in the joint shafts 48 and spaced a certain distance from the pulleys 50*a*, 50*b*, 50*c* and the gears 55, are not wound around the pulleys 50*a*, 50*b*, 50*c* and the gears 55 and do not need to be flexible even when the wires 54*a*, 54*b*, 54*c* are moved back and forth in a reciprocating range L (see FIG. 5). Therefore, elongation of the wires 54*a*, 54*b*, 54*c* while being driven or due to aging deterioration can be minimized. Consequently, at the time the pulleys 50*a*, 50*b*, 50*c* are rotated, the wires 54*a*, 54*b*, 54*c* are actuated highly responsively and accurately to operate the distal-end working unit 12 accurately. In other words, the wires 54*a*, 54*b*, 54*c*, which serve as power transmitting members, have first portions (bare portions of the wires 54*a*, 54*b*, 54*c*) that are flexible and second portions (reinforced portions of the wires 54*a*, 54*b*, 54*c*) that are more rigid than the first portions. The wires 54*a*, 54*b*, 54*c* thus constructed can easily be wound around the pulleys 50*a*, 50*b*, 50*c* and can yet be actuated highly accurately with a high response because of minimized stretching.

The actuator block 30 houses therein three motors 40*a*, 40*b*, 40*c* corresponding to respective mechanisms of three degrees of freedom which are incorporated in the distal-end working unit 12. The motors 40*a*, 40*b*, 40*c* are arrayed parallel to each other in the longitudinal direction of the connector 15. The motors 40*a*, 40*b*, 40*c* engage the respective pulleys 50*a*, 50*b*, 50*c*. The actuator block 30 is disposed downwardly of the end of the operation command unit 14 in the Z1 direction. The motors 40*a*, 40*b*, 40*c* can be energized to rotate under the control of the controller 45 based on the operation of the trigger lever 32 and the composite input unit 34. When the motors 40*a*, 40*b*, 40*c* are energized, their drive forces are transmitted to the pulleys 50*a*, 50*b*, 50*c*, which move the wires 54*a*, 54*b*, 54*c* along their longitudinal axes to transmit the drive forces to the distal-end working unit 12, which is operated. The actuator block 30 and the connector 15, i.e., the motors 40*a*, 40*b*, 40*c* and the pulleys 50*a*, 50*b*, 50*c*, function as a drive mechanism for imparting the drive forces to the wires 54*a*, 54*b*, 54*c* as the power transmitting members to operate the distal-end working unit 12.

As shown in FIGS. 2, 4, and 5, the joint shaft 48 houses therein six wires (because each of three wires 54*a*, 54*b*, 54*c* is looped back), a cleaning tube 58 through which a cleaning solution such as water and an enzyme detergent flows, and a disk-shaped sealing member 64 which divides the interior space of the joint shaft 48 into a compartment near the distal-end working unit 12 and a compartment near the connector 15, i.e., the drive mechanism.

Figure 6:
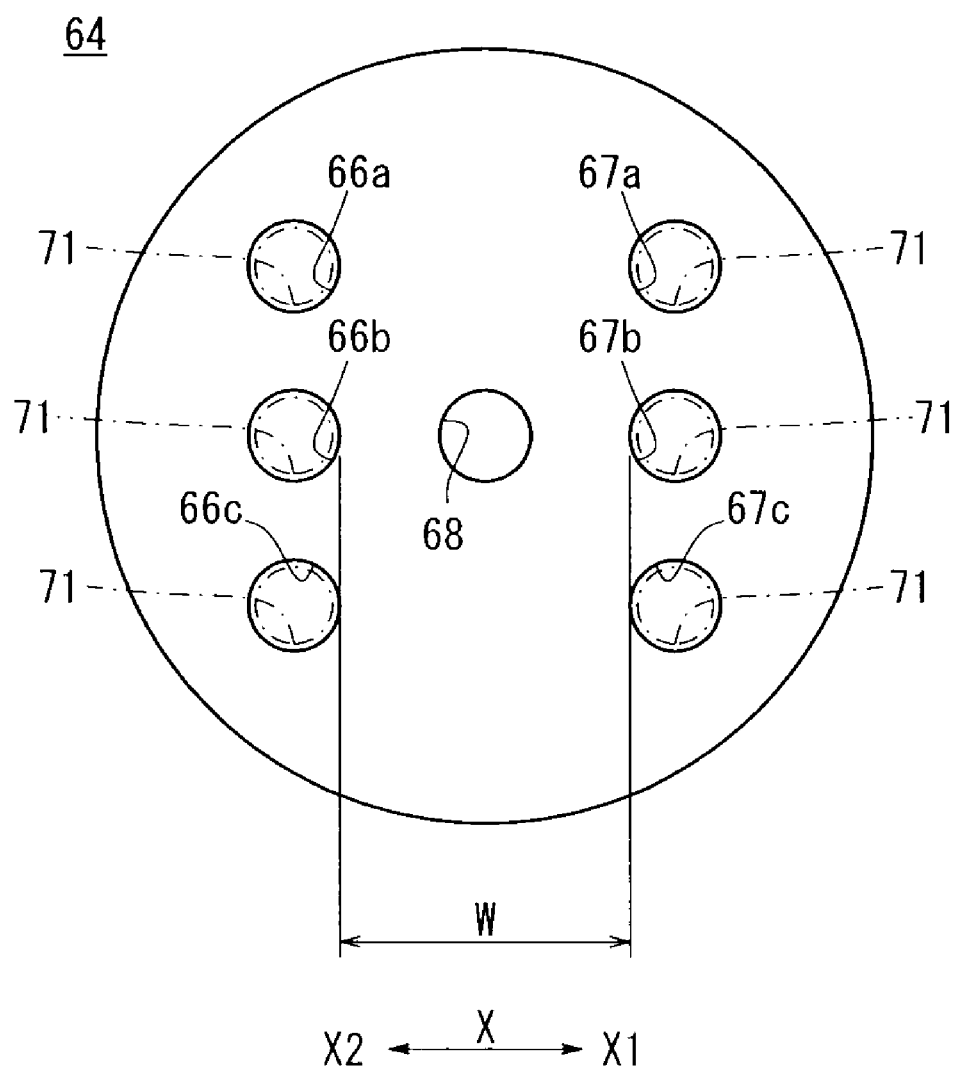
FIG. 6 is a front view of the seal member.

As shown in FIGS. 4 and 6, the six stretches of the wires 54*a*, 54*b*, 54*c* and the cleaning tube 58 extend through respective holes 66*a*, 67*a*, 66*b*, 67*b*, 66*c*, 67*c*, 68 defined in the sealing member 64.

The cleaning tube 58 has a cleaning solution inlet 70 (see FIG. 2) mounted on a rear surface 59 of the distal end portion of the connector 15 and opening in the Z2 and a cleaning solution outlet 72 disposed in the compartment near the distal-end working unit 12 and opening from the sealing member 64 toward the distal-end working unit 12. The cleaning tube 58 is made of rubber, silicone, or a fluororesin such as PTFE (polytetrafluoroethylene) or the like. In the present embodiment, the cleaning tube 58 is curved out of contact with the pulleys 50*a*, 50*b*, 50*c* in the connector 15, and extends substantially centrally among the stretches of the wires 54*a*, 54*b*, 54*c* in the joint shaft 48.

As shown in FIG. 2, the cleaning solution inlet 70 of the cleaning tube 58 is usually closed by a plug 69 when the manipulator 10 is not to be cleaned. When the connector 15 is mounted on the actuator block 30, the cleaning solution inlet 70 that is closed by the plug 69 is positioned in a clearance, not shown, in the actuator block 30. When the cleaning tube 58 is to be used, i.e., when the manipulator 10 is to be cleaned, the connector 15 is dismounted from the actuator block 30, the plug 69 is removed, and the cleaning solution is introduced from the cleaning solution inlet 70 into the cleaning tube 58. The cleaning solution flows through the cleaning tube 58 in the Z1 direction and is ejected from the cleaning solution outlet 72 into the joint shaft 48. To eject the cleaning solution effectively from the cleaning solution outlet 72, the cleaning solution outlet 72 may be of a flat shape or the cleaning solution outlet 72 may be closed and a number of small holes may be defined in the circumferential wall of the cleaning tube 58 near the cleaning solution outlet 72. The flat cleaning solution outlet 72 has a reduced open area and hence serves as a check valve for reducing a flow of blood tending to flow into the cleaning tube 58.

As shown in FIGS. 4 and 5, the cleaning solution outlet 72 is positioned in the Z directions at a location for cleaning the interior of the distal-end working unit 12 and the interior of the joint shaft 48 which extends from the sealing member 64 in the Z1 direction. The cleaning solution outlet 72 is separated away from the sealing member 64 in the Z1 direction. The cleaning tube 58 does not necessarily project from the sealing member 64 toward the distal-end working unit 12. For example, the distal end of the cleaning unit 58 may be fixed in the hole 68, so that the opening of the hole 68 which is open toward the distal-end working unit 12 may serve as the cleaning solution outlet 72.

The sealing member 64 is in the form of a shield wall having an outer circumferential surface closely held against an inner circumferential surface of the joint shaft 48 and dividing the interior space of the joint shaft 48 into the compartment near the distal-end working unit 12 and the compartment near the connector 15, i.e., the drive mechanism, for thereby preventing fluids from flowing between the compartments. The sealing member 64 has an outside diameter selected to hold the outer circumferential surface thereof closely against the inner circumferential surface of the joint shaft 48. The sealing member 64 has a thickness in the Z directions which is large enough to keep itself stably in the joint shaft 48. The sealing member 64 may be located within the distal-end working unit 12 remotely from the joint shaft 48 in the Z1 direction. The sealing member 64 is made of rubber, silicone, or a fluororesin such as PTFE or the like, and is in the shape of a disk whose diameter corresponds to the inside diameter of the joint shaft 48.

As shown in FIGS. 4 and 6, the sealing member 64 has the holes 66a, 67a through which the stretches of the wire 54a pass, the holes 66b, 67b through which the stretches of the wire 54b pass, the holes 66c, 67c through which the stretches of the wire 54c pass, and the hole 68 through which the cleaning tube 58 passes. These holes 66a, 67a, 66b, 67b, 66c, 67c, 68 have their axes extending in the Z directions. If the distal-end working unit 12 has two degrees of freedom or four or more degrees of freedom, and the number of wires used as power transmitting members is correspondingly changed, then the number of holes in the sealing member 64 is also changed.

The holes 66a, 67a, the holes 66b, 67b, and the holes 66c, 67c are spaced from each other by a distance W (see FIG. 6) which is equal to the outside diameter of the pulleys 50a, 50b, 50c to keep the wires 54a, 54b, 54c out of contact with the inner wall surfaces and edges of the holes 66a, 67a, 66b, 67b, 66c, 67c. Since any frictional resistance that the wires 54a, 54b, 54c receive from the inner wall surfaces and edges of the holes 66a, 67a, 66b, 67b, 66c, 67c is reduced, the wires 54a, 54b, 54c can move smoothly through these holes. The positions in the Y directions at which the wires 54a, 54b, 54c are wound around the pulleys 50a, 50b, 50c are aligned with the positions in the Y directions of the holes 66a, 67a, 66b, 67b, 66c, 67c, also reducing any frictional resistance that the wires 54a, 54b, 54c receive from the inner wall surfaces and edges of the holes 66a, 67a, 66b, 67b, 66c, 67c.

When the wires 54a, 54b, 54c move reciprocatingly in the Z directions through the holes 66a, 67a, 66b, 67b, 66c, 67c, the wires 54a, 54b, 54c tend to slide against the inner wall surfaces of the holes 66a, 67a, 66b, 67b, 66c, 67c. Therefore, each of the inner wall surfaces of the holes 66a, 67a, 66b, 67b, 66c, 67c may have a lubricating layer 71 (see the two-dot-and-dash lines in FIG. 6), such as a PTFE pipe or coating for reducing frictional resistance to allow the wires 54a, 54b, 54c to move smoothly through the holes 66a, 67a, 66b, 67b, 66c, 67c.

As shown in FIG. 5, the sealing member 64 is inserted from the distal end of the joint shaft 48 into the joint shaft 48 until the sealing member 64 abuts against an end face, which faces in the Z1 direction, of an annular ridge 82 on an inner circumferential surface of the joint shaft 48. Then, a ring 84 is press-fitted into the joint shaft 48 and held against an end face, which faces in the Z1 direction, of the sealing member 64. The sealing member 64 is therefore sandwiched in place between the annular ridge 82 and the ring 84. The ring 84 may be bonded or welded to the inner circumferential surface of the joint shaft 48. The annular ridge 82 may similarly be in the form of a ring bonded or welded to the inner circumferential surface of the joint shaft 48.

Figure 8:
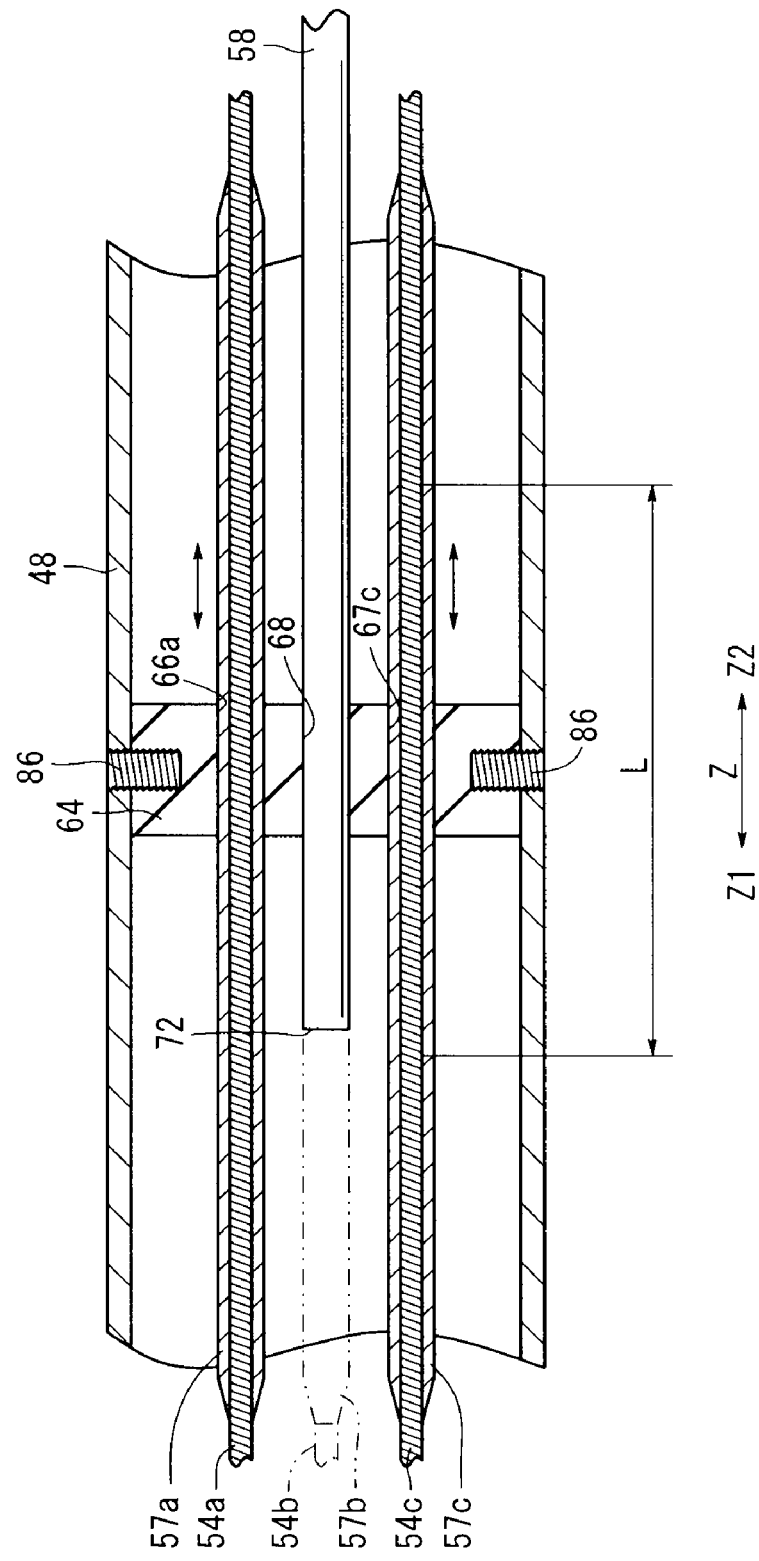
FIG. 8 is a cross-sectional view of a modified structure by which a seal member is fixed.

As shown in FIG. 8, the sealing member 64 may be fixed to the joint shaft 48 by small-diameter screws 86 which are threaded radially inwardly through the joint shaft 48 into the sealing member 64. Alternatively, the sealing member 64 may be fixed to the joint shaft 48 by small-diameter pins 86. The sealing member 64 may simply be bonded or welded to the inner circumferential surface of the joint shaft 48, insofar as it will not be displaced in the Z directions when the wires 54a, 54b, 54c are actuated.

As shown in FIG. 2, the actuator block 30 has two independent engaging fingers 210 for holding the connector 15 and three alignment pins 212 for positioning and holding the connector 15.

The alignment pins 212 are mounted on the upper surface of the actuator block 30 in alignment with respective three fitting holes 206 defined in the connector 15, and extend in the Y1 direction. Since the actuator block 30 has the three alignment pins 212, the connector 15 is supported by the actuator block 30 at the three positions corresponding to the alignment pins 212 and is simply and reliably positioned with respect to the actuator block 30.

For connecting the connector 15 to the actuator block 30, the operator displaces the connector 15 in the Y2 direction toward the actuator block 30 in order to have the alignment pins 212 inserted respectively into the respective fitting holes 206. As the connector 15 is displaced further toward the actuator block 30, the engaging fingers 210 are slightly displaced outwardly by tapered distal ends thereof which slide on the outer surfaces of engaging teeth 207 on the connector 15. When the lower surface of the connector 15 engages the upper surface of the actuator block 30, the engaging fingers 210 fully engage the engaging teeth 207, whereupon the connector 15 is completely mounted on the actuator block 30. For removing the connector 15 from the actuator block 30, the engaging teeth 207 are manually operated in an opening direction, and the connector 15 is lifted in the Y1 direction away from the actuator block 30.

The operation command unit 14, which is part of the input means for operating the distal-end working unit 12 of the manipulator 10, will be described below.

The operation switch 35 serves as input means to selectively enable or disable the manipulator 10. The LED 29 serves as an indicator for indicating a controlled state of the manipulator 10. The LED 29 is of a size large enough to be easily visually recognizable by the operator, and yet is sufficiently small and light not to interfere with the operation of the manipulator 10. The LED 29 is located in a visually recognizable position substantially centrally on the upper surface of the bridge 28, in juxtaposed relation to the operation switch 35. The LED 29 is turned on in synchronism with the operation switch 35 when it is turned on. Therefore, when the operator turns on the operation switch 35, the operator can reliably recognize and confirm the turn-on of the operation switch 35 by visually checking the LED 29.

The composite input unit 34 serves as a composite input means for giving rotational commands in rolling directions (shaft rotating directions) and yawing directions (left and right directions) to the distal-end working unit 12.

Figure 7:
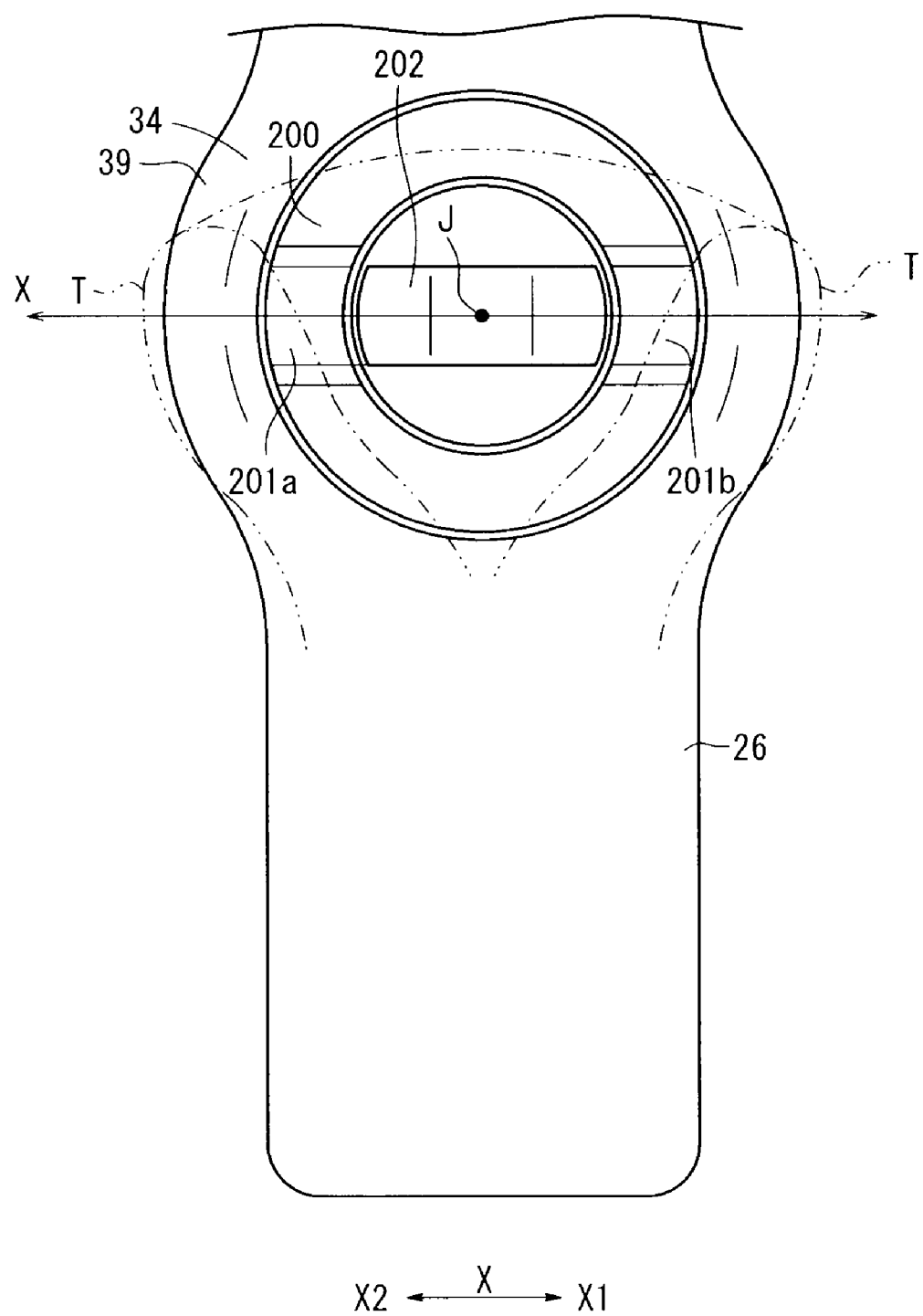
FIG. 7 is a view showing the surface of a composite input unit.

As shown in FIG. 7, the composite input unit 34 is of a circular shape when viewed in front elevation and is provided on a flat area 39 of the joint between the upper end of the grip handle 26 and the bridge 28. As can be seen from FIG. 1, the composite input unit 34 is disposed in a position where it can easily be operated by the thumb of the hand which is gripping the grip handle 26. The flat area 39 is of a substantially annular shape that is larger in diameter than the composite input unit 34. When the composite input unit 34 is not to be operated, the operator places the thumb on the flat area 39, so that the operator can firmly grip the grip handle 26 without touching the composite input unit 34. A line normal to the flat area 39 and the surface of the composite input unit 34 extends along a direction which lies substantially intermediate between the Z2 direction and the Y1 direction. Therefore, the operator can have the finger pad T of the thumb held naturally against the flat area 39 and the surface of the composite input unit 34.

As shown in FIG. 7, the composite input unit 34 includes a shuttle ring 200 disposed in the flat area 39 and a pad 202 disposed inside the shuttle ring 200 and projecting outwardly.

The shuttle ring 200 includes a pair of knobs 201a, 201b disposed as finger rests in diametrically symmetric positions. The shuttle ring 200 serves as an input means for giving rotational commands in rolling directions to the distal-end working unit 12. When the shuttle ring 200 is turned a greater angular interval by operation of the knobs 201a, 201b, the distal-end working unit 12 is rotated at a higher speed. When the shuttle ring 200 is not turned, the distal-end working unit 12 is held at rest in rolling directions.

The shuttle ring 200 is angularly movable about the axis J in an angular movable range of, for example, ±10° from a standard position (neutral position or original position) thereof. The angular movable range of the shuttle ring 200 should preferably be large enough to allow the shuttle ring 200 to move a certain distance for better operability, e.g., for entering delicate actions, and should preferably be kept within the movable range of the finger pad T of the thumb for natural and comfortable operation of the shuttle ring 200 by the thumb.

The pad 202 serves as an input means for giving tilting commands in yawing directions to the distal-end working unit 12. When the pad 202 is pushed a greater interval, the distal-end working unit 12 is tilted at a higher speed. When the pad 202 is not pushed, the distal-end working unit 12 is held at rest in yawing directions. The pad 202 comprises a projection having upper and lower straight surfaces extending parallel to each other and left and right arcuate ends which are convex radially outwardly, as viewed in front elevation. The left and right arcuate ends of the pad 202 have a radius of curvature such that the left and right arcuate ends are complementary in shape to the circular inner surface of the shuttle ring 200.

The pad 202 is easily tilted in right and left pushing directions when each of the right and left surfaces thereof is pushed by the thumb. When the pad 202 is not tilted, it is automatically returned to its standard position under the bias of resilient members, not shown.

Input actions applied to the shuttle ring 200 and the pad 202 to turn and push them are detected by pressure-sensitive sensors or the like, not shown, disposed in the casing of the operation command unit 14. Based on detected signals from the pressure-sensitive sensors, the motors 40a, 40b, 40c are energized through an unillustrated control means such as a circuit board to cause the pulleys 50a, 50b, 50c to actuate the wires 54a, 54b, 54c for thereby operating the distal-end working unit 12.

Structural and operational details of the trigger lever 32 will be described below.

As shown in FIG. 1, the trigger lever 32 is disposed slightly below the bridge 28 and projects in the Z1 direction. The trigger lever 32 is disposed in such a position that it can easily be operated by the index finger of the hand that is gripping the grip handle 26.

The trigger lever 32 is operatively coupled to the grip handle 26 by an arm 98, and is movable toward and away from the grip handle 26. The arm 98 is operatively connected to a sensor, not shown, disposed in the grip handle 26. The distance that the trigger lever 32 has moved toward or away from the grip handle 26 is detected by the sensor, which supplies a signal representing the detected distance to the controller 45. The trigger lever 32 serves as an input means for giving commands for opening and closing the gripper 60 to the distal-end working unit 12.

The trigger lever 32 can be pulled toward the grip handle 26 (i.e., in the Z2 direction) by the finger held thereagainst, and can be pushed away from the grip handle 26 in the Z1 direction by the finger held thereagainst. When the trigger lever 32 is thus pulled or pushed, the sensor associated therewith gives opening and closing commands to the gripper 60.

The switch 36, which is spaced from the trigger lever 32 in the Y2 direction, comprises an alternate switch. When the switch 36 is operated, it keeps the gripper 60 in a state caused by operation of the trigger lever 32, i.e., an open state or closed state.

Operation of the thus-constructed manipulator 10 according to the present embodiment will be described below.

As shown in FIG. 3, the distal-end working unit 12 has the mechanisms of three degrees of freedom representing a roll axis, a yaw axis, and a gripper axis, and has a plurality of joints with gaps A defined therein. Even if the distal-end working unit 12 has a single mechanism of one degree of freedom, it has a joint. Therefore, while the surgeon is performing a surgical operation on the patient, the blood and body fluids in the body cavity 22 of the patient flow through the gaps A into the joint shaft 48. If the blood and body fluids flowed deeply into the joint shaft 48 in the Z2 direction and the drive mechanisms in the connector 15 (the cover 37), then it would be tedious and time-consuming to clean and sterilize the manipulator 10 after the surgical operation.

According to the present embodiment, the joint shaft 48 houses therein the sealing member 64 which divides the interior space of the joint shaft 48 into the compartment near the distal-end working unit 12 and the compartment near the connector 15. The blood and body fluids which have entered through the gaps A in the distal-end working unit 12 and then flow along the inner circumferential surface of the joint shaft 48 from the distal-end working unit 12 toward the connector 15 are prevented from flowing into the connector 15 by the sealing member 64. Consequently, during the surgical operation, the blood and body fluids are prevented from flowing deeply into the joint shaft 48 and also into the connector 15.

The manipulator 10 can thus be cleaned and sterilized easily, i.e., serviced for maintenance easily. Owing to the sealing member 64, in addition to the liquid-tightness, gas-tightness is also secured to block flowing of gas such as air. Thus, air hardly leaks from the interior of the joint shaft 48 on the distal end working unit 12 side of the sealing member 64, that is, the inside air is nearly sealed in the joint shaft 48, and the nearly-sealed air functions as a seal for the joint shaft 48. Owing to the nearly-sealed air, the blood and body fluids are prevented from entering the interior of the joint shaft 48 through the gaps A, to a maximum extent. In other words, in the manipulator 10, the sealing member 64 effectively prevents the blood and body fluids from entering the interior of the joint shaft 48 and the connector 15, and the pulleys 50a, 50b, 50c disposed in the connector 15 do not need to be cleaned, or the pulleys can be cleaned with ease. The connector 15 may have a cleaning solution inlet hole for introducing the cleaning solution into the connector 15 to clean the interior thereof and also a cleaning solution outlet hole for discharging the cleaning solution out of the connector 15.

As shown in FIG. 5, the cleaning solution outlet 72 of the cleaning tube 58 is disposed in the compartment near the distal-end working unit 12 and opening away from the sealing member 64 toward the distal-end working unit 12. When the manipulator 10 is to be cleaned, the plug 69 is removed and the cleaning solution is introduced from the cleaning solution inlet 70 into the cleaning tube 58. Therefore, the interior of the joint shaft 48 and the interior of the distal-end working unit 12 can easily be cleaned. Alternatively, a tube and a syringe, not shown, may be connected to the distal-end working unit 12 or the cleaning solution inlet 70 of the cleaning tube 58, and the syringe may be operated to pump the cleaning solution into the joint shaft 48 and the distal-end working unit 12 for cleaning.

The blood and body fluids may flow through the gaps A into contact with the sealing member 64 and then flow back through the gaps A into the body cavity 22. In view of such a fluid flow, the sealing member 64 should preferably be made of a biocompatible material such as rubber, silicone, or a fluororesin, as described above. For the same reason, the cleaning tube 58 should preferably be made of the same maternal as the sealing member 64.

As shown in FIG. 5, when the wires 54a, 54b, 54c are actuated in the reciprocating range L, the reinforcing tubes 57a, 57b, 57c surrounding the respective wires 54a, 54b, 54c slide through the holes 66a, 67a, 66b, 67b, 66c, 67c at all times.

Usually, each of the wires 54a, 54b, 54c comprises a cord of twisted strands for desired mechanical strength. Therefore, if the cords were directly placed in the holes 66a, 67a, 66b, 67b, 66c, 67c, clearances would be developed between the wires 54a, 54b, 54c and the inner wall surfaces of the holes 66a, 67a, 66b, 67b, 66c, 67c tending to allow the blood and body fluids to flow therethrough and hence through the sealing member 64. According to the present embodiment, since the reinforcing tubes 57a, 57b, 57c are disposed in the corresponding holes 66a, 67a, 66b, 67b, 66c, 67c at all times, the blood and body fluids are effectively blocked by the sealing member 64. Also, since the sealing member 64 further improves gas-tightness, the air in the joint shaft 48 prevents more reliably the blood and body fluids from entering the interior of the joint shaft 48. Even if the bare portions of the wires 54a, 54b, 54c are disposed in the holes 66a, 67a, 66b, 67b, 66c, 67c, the sealing member 64 is still effective to block the blood, body fluids and air to some extent particularly when the manipulator 10 is used under certain conditions.

Figure 9:
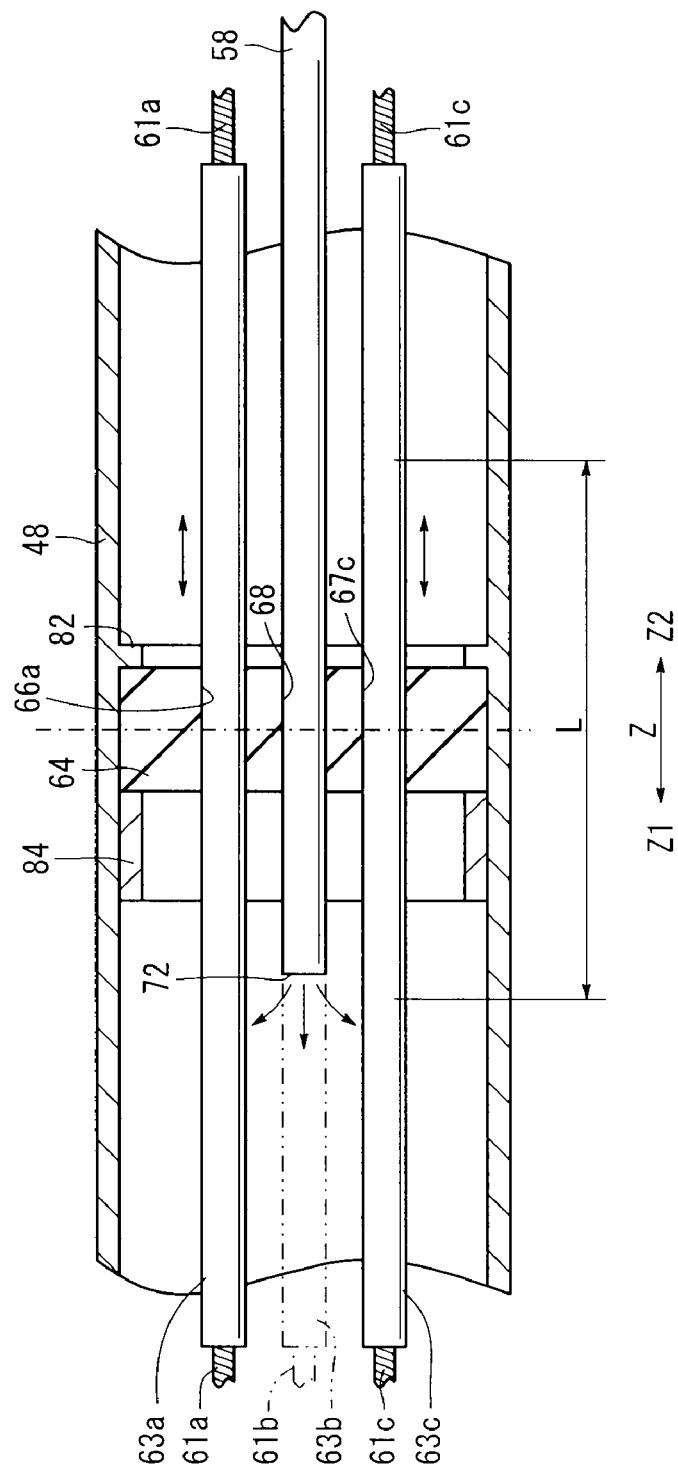
FIG. 9 is a cross-sectional view of wires and reinforcing tubes according to a modification.

According to the modification shown in FIG. 9, rather than the reinforcing tubes 57a, 57b, 57c, bar members 63a, 63b, 63c made of metal, etc. extend through the holes 66a, 67a, 66b, 67b, 66c, 67c in the sealing member 64, and wires 61a, 61b, 61c, which are of the same material as the wires 54a, 54b, 54c, are coupled to the ends of the bar members 63a, 63b, 63c. The bar members 63a, 63b, 63c serve as second portions that are more rigid than the wires 61a, 61b, 61c which serve as first portions. Since the bar members 63a, 63b, 63c are positioned to slide against the inner wall surfaces of the holes 66a, 67a, 66b, 67b, 66c, 67c, the sealing member 64 provides a high sealing capability.

Further, instead of a combination of the wires and the reinforcing tubes or a combination of the wires and the bar members, for example, metal rods (not shown) may be used. In this case, when the surfaces of the rods are lubricated, liquid-tightness and gas-tightness can be maintained between the rods and the sealing member even if the reinforcing tubes or the bar members are not disposed at the sliding contact portions with the sealing member. The rods should preferably be applied to a structure in which the rods are moved backward and forward with an operating unit such as a trigger lever 32 or with a linear motor (not shown). Even when the rods are used, portions that engage with pulleys or gears are formed of wires.

The cleaning solution outlet 72 at the distal end of the cleaning tube 58 is open in the joint shaft 48, whereas the cleaning solution inlet 70 of the cleaning tube 58 is closed by the plug 69 during the surgical operation. During the surgical operation, therefore, the internal pressure in the cleaning tube 58 is kept at a certain level for preventing the blood and body fluids from entering the cleaning tube 58 through the cleaning solution outlet 72. Furthermore, inasmuch as the gas, e.g., carbon dioxide, in the body cavity is also prevented from leaking out through the cleaning tube 58, the internal pressure in the body cavity is kept constant.

As shown in FIG. 2, instead of the plug 69, a check valve 80 (indicated by the broken lines in FIG. 2) may be connected to the cleaning tube 58 near the cleaning solution inlet 70 for blocking a fluid flow from the cleaning solution outlet 72 to the cleaning solution inlet 70 (in the Z2 direction). As with the plug 69, the check valve 80 is effective to prevent back-flow of the blood, body fluids, and gas through the cleaning solution outlet 72. In addition, since the plug 69 does not need to be attached and detached, the manipulator 10 is easier to handle.

Depending on the specifications of the manipulator 10, the cleaning tube 58 may be dispensed with. For example, if the interior of the joint shaft 48 is to be cleaned from the side of the distal-end working unit 12, then the cleaning tube 58 is not required. In this case, the manipulator 10 is simpler in structure.

Figure 10C:
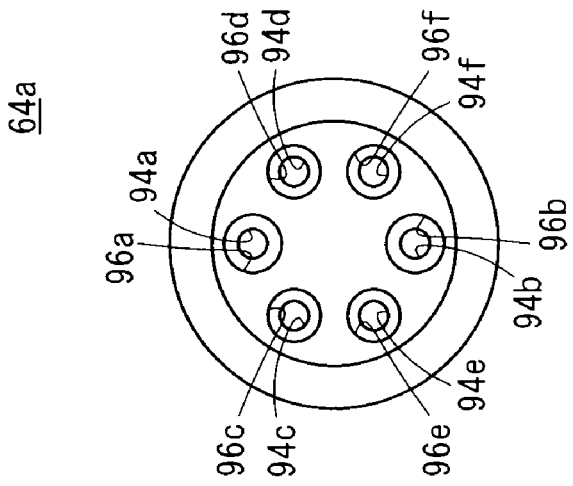
FIG. 10C is a rear view of the sealing member shown in 10A.
Figure 10B:
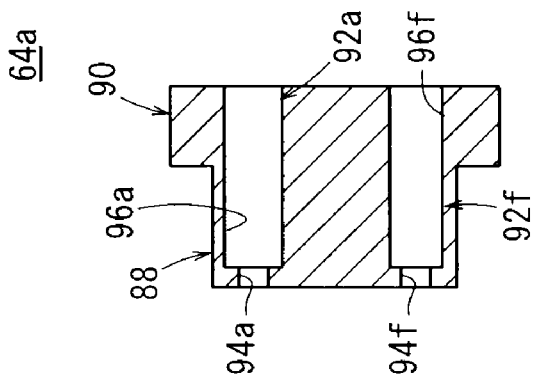
FIG. 10B is a cross-sectional view taken along line XB-XB of FIG. 10A.
Figure 10A:
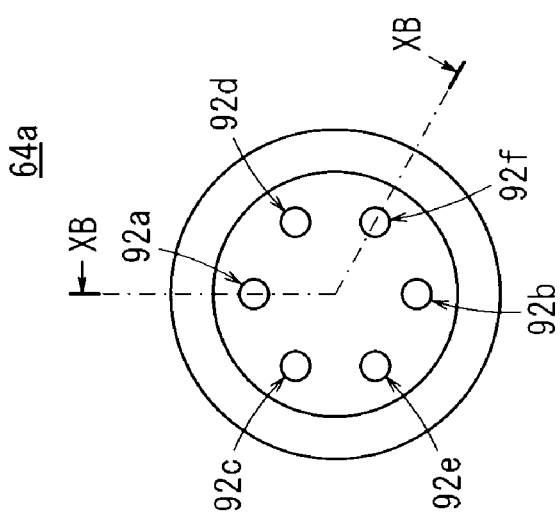
FIG. 10A is a front view of a sealing member according to a modification of the sealing member shown in FIG. 4.

FIGS. 10A to 10C illustrate a sealing member 64a according to a modification of the sealing member 64 shown in FIG. 4.

The sealing member 64a is formed into a stepped cylindrical shape having a small-diameter portion 88 and a large-diameter portion 90. The outer circumferential surface of the large-diameter portion 90 is held in close contact with the inner circumferential surface of the joint shaft 48, thereby dividing the interior of the joint shaft 48 into two. As with the sealing member 64, the sealing member 64a has holes 92a, 92b, 92c, 92d, 92e, 92f which extend therethrough in the Z directions and through which the wires are inserted. Each of the holes 92a to 92f is formed into a stepped shape, and in other words, consists of a small hole 94a, 94b, 94c, 94d, 94e, 94f and a large hole 96a, 96b, 96c, 96d, 96e, 96f. The small holes 94a to 94f extend from the end face (end face of the sealing member 64a on the Z1 side) of the small-diameter portion 88. The large holes 96a to 96f extend from the end face (end face of the sealing member 64a on the Z2 side) of the large-diameter portion 90, and are joined to the small holes 94a to 94f, respectively.

The small holes 94a to 94f have such an inner diameter as corresponds to the diameter of the reinforcing tubes 57a to 57c (see FIG. 5) or the bar members 63a to 63c (see FIG. 9), i.e., such an inner diameter that the small holes 94a to 94f can be held in sliding contact with the reinforcing tubes 57a to 57c or the bar members 63a to 63c so as to secure liquid-tightness and gas-tightness. The large hole 96a to 96f has a diameter larger than that of the small hole 94a to 94f. Thus, even if reciprocation of the wires 54a to 54c causes a winding position of the wires onto the pulleys 50a to 50c to be shifted in the X directions or the Y directions, the wires 54a to 54c (reinforcing tubes 57a to 57c) which slidingly contact with the small holes 94a to 94f are prevented from abutting against an edge of an opening end on the Z2 side of the large holes 96a to 96f.

Hereinafter, explanations will be made concerning a case where the sealing member 64a is applied to a hybrid type of manipulator in which two wires 54a, 54b, motors 40a, 40b, and pulleys 50a, 50b are used to electrically move the distal-end working unit 12 in rolling directions and yawing directions, and unillustrated rods (e.g., metal rods) are moved forward and backward by operations of the trigger lever 32 (alternatively, an unillustrated rocking lever or the like) to mechanically open and close the gripper 60. In this case, the above-mentioned rods, which are manually-driven, may be inserted through a pair of upper and lower holes 92a, 92b, and the wires 54a, 54b (reinforcing tubes 57a, 57b), which are electrically-driven, may be inserted through the rest of the holes 92c to 92f. At least portions of the rods that slidingly contact with the holes 92a, 92b should preferably be coated with a lubricative coat, and the same applies to the bar members 63a to 63c. As a matter of course, the inner surfaces of the holes 92a to 92f (small holes 94a to 94f) may be coated with lubricating layers 71 (see FIG. 6).

As with the sealing member 64 shown in FIG. 6, a hole 68 may be formed centrally in the sealing member 64a, and a cleaning tube 58 may be inserted through the hole 68.

Figure 11:
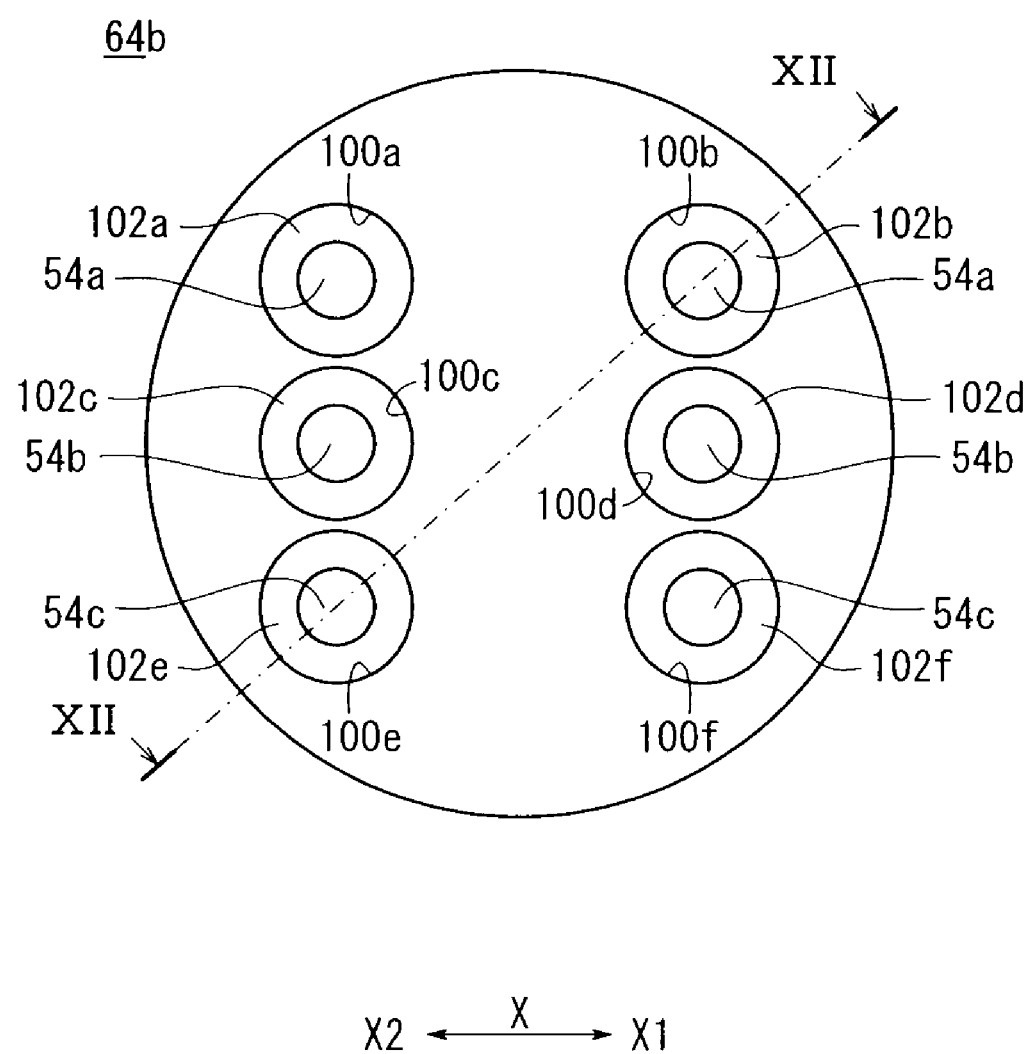
FIG. 11 is a front view of a sealing member according to another modification of the sealing member shown in FIG. 4.
Figure 12:
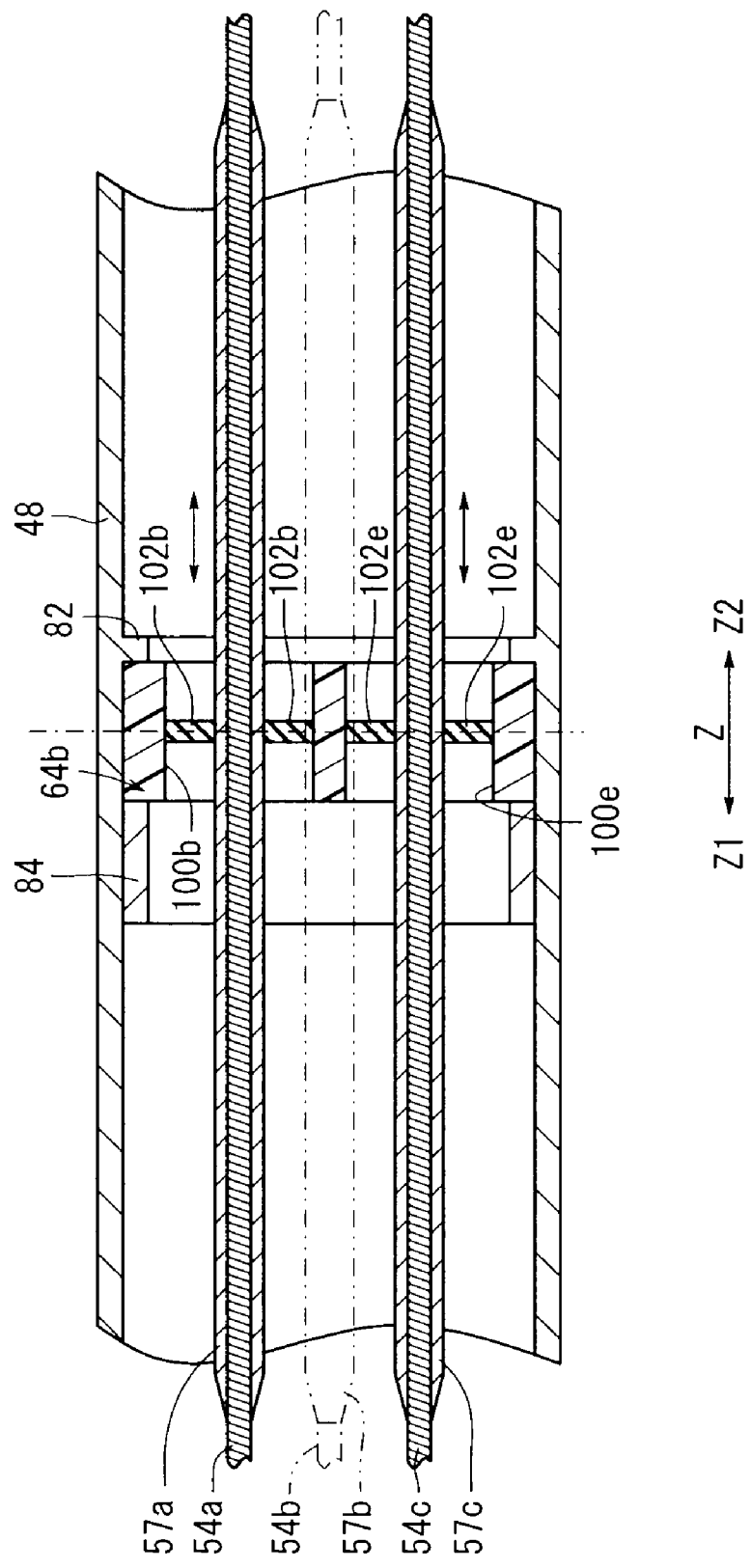
FIG. 12 is a cross-sectional view taken along line XII-XII.

FIG. 11 is a front view of a sealing member 64b according to another modification, and FIG. 12 is a cross-sectional view taken along with line XII-XII shown in FIG. 11.

As shown in FIGS. 11 and 12, the sealing member 64b has holes 100a to 100f formed by widening the holes 66a to 66c, 67a to 67c in the sealing member 64 (see FIG. 6). Each of the holes 100a to 100f has a partition member (elastic member, elastic membrane) 102a to 102f fixed on the inner circumference thereof, the partition member 102a to 102f being made of an elastic material such as rubber. Each partition member 102a to 102f has a smaller hole centrally, and each of the wires 54a to 54c (reinforcing tubes 57a to 57c) is inserted through and fixed with respect to the smaller hole. That is, a partition member 102a to 102f serving as a partition wall is provided for each wire.

Figure 13A:
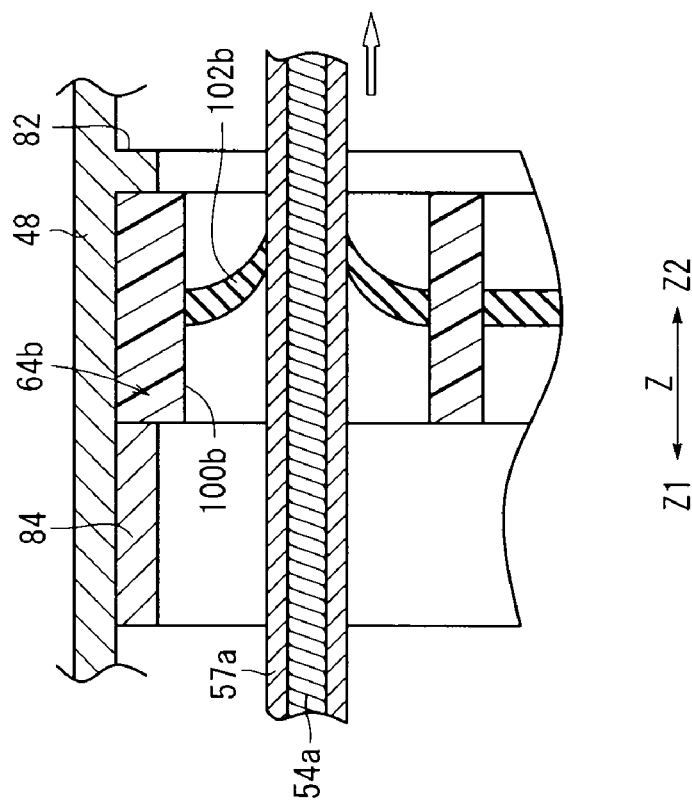
FIG. 13A is a cross-sectional view illustrating a state where the sealing member shown in FIG. 11 is tensioned by movement of a wire.
Figure 13B:
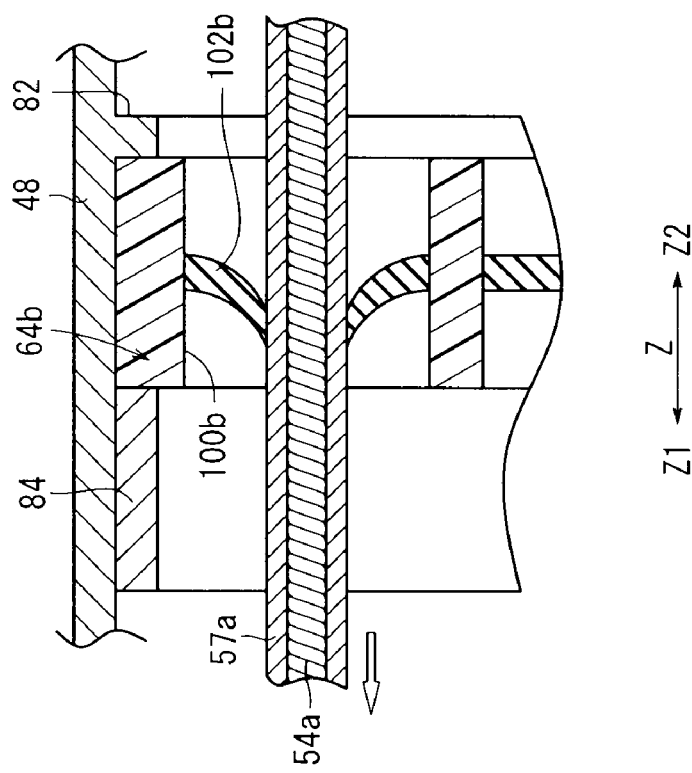
FIG. 13B is a cross-sectional view illustrating a state where the wire is moved in a direction different from the direction shown in FIG. 13A.

Thus, as shown in FIGS. 13A and 13B, in the sealing member 64b, for example, when the wire 54 is reciprocated through the holes 100b, the partition member 102b is elastically stretched, thereby to secure liquid-tightness and gas-tightness between both sides of the sealing member 64b.

Since the above sealing member 64b has no contact portion which slidingly contacts with the wires 54a to 54c, force required to move the wires 54a to 54c is reduced. Thus, the motors 40a to 40c can be reduced in size, and accordingly, the entire manipulator 10 can be reduced in size. Force required to move the wires 54a to 54c against elastic force of the partition members 102a to 102f depends on a displacement of the wires and properties of the rubber or the like of the partition members 102a to 102f. The rubber of the partition members 102a to 102f should preferably comprise silicone rubber or fluorine-containing rubber, in view of contact with blood, body fluids or the like.

Figure 14:
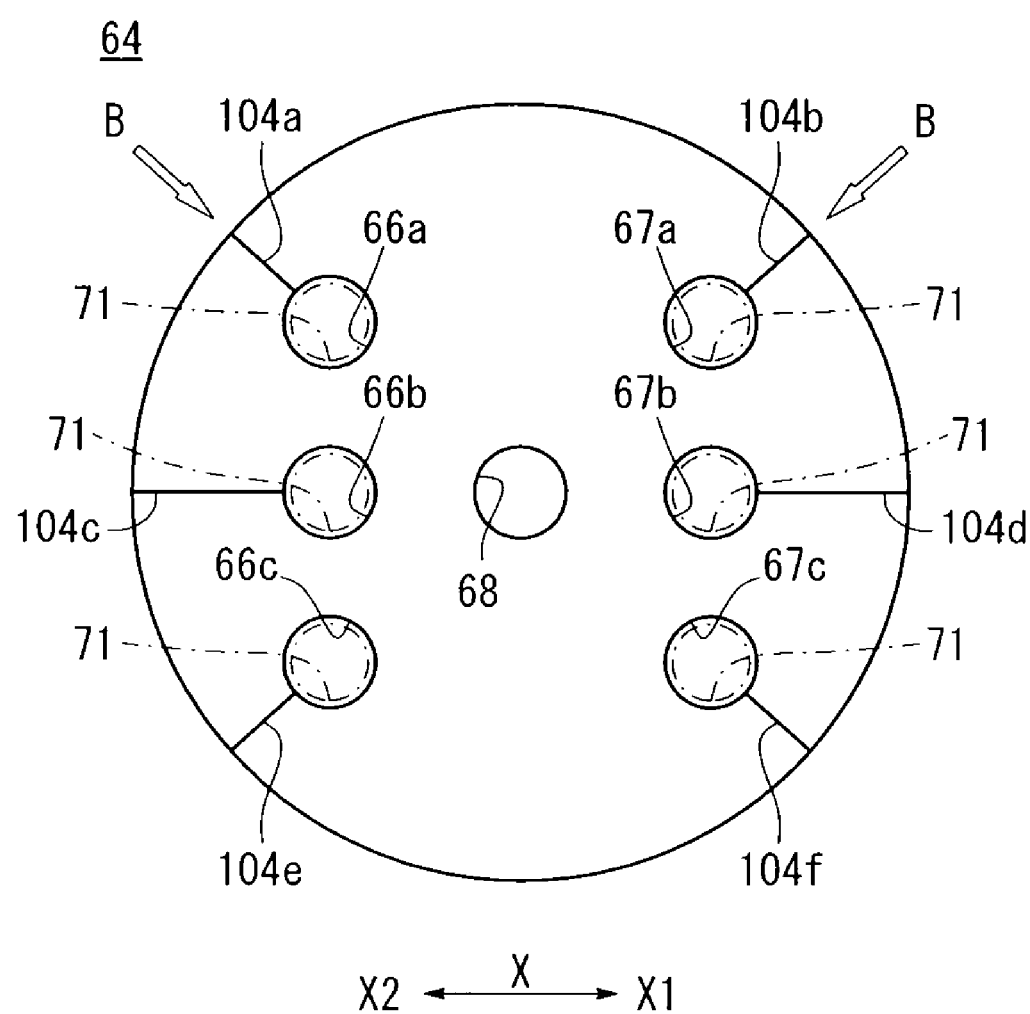
FIG. 14 is a front view of a modification in which slits are formed in the sealing member shown in FIG. 4.

As shown in FIG. 14, slits 104a to 104f may be formed by making incisions in the sealing member 64 (see FIG. 6) from the outer circumferential surface to the holes 66a to 66c, 67a to 67c. In the sealing member 64a shown in FIG. 10A, such slits 104a to 104f may be formed similarly. If the slits 104a to 104f are provided, at times when the manipulator 10 is assembled, e.g., when the wires 54a to 54c are wound between the pulleys 50a to 50c and gears 55, the wires 54a to 54c are firstly looped, and the looped wires 54a to 54c are then inserted through the slits 104a to 104f into the holes 66a to 66c, 67a to 67c. Thus, the manipulator is easily assembled, compared to the case where the wires 54a to 54c are firstly inserted through the holes 66a to 66c, 67a to 67c, and the wires 54a to 54c are then looped. For example, the wire 54a is inserted through the slits 104a, 104b in a direction indicated by arrow B in FIG. 14, whereby the wire 54a is easily inserted into the holes 66a, 67a.

Even when the slits 104a to 104f are formed, the slits 104a to 104f are hermetically closed at a time when the sealing member 64 is fitted into the joint shaft 48, and thus, the sealing member can maintain sealing performance. Alternatively, after the wires have been inserted, the slits may be closed using an adhesion bond.

Figure 15:
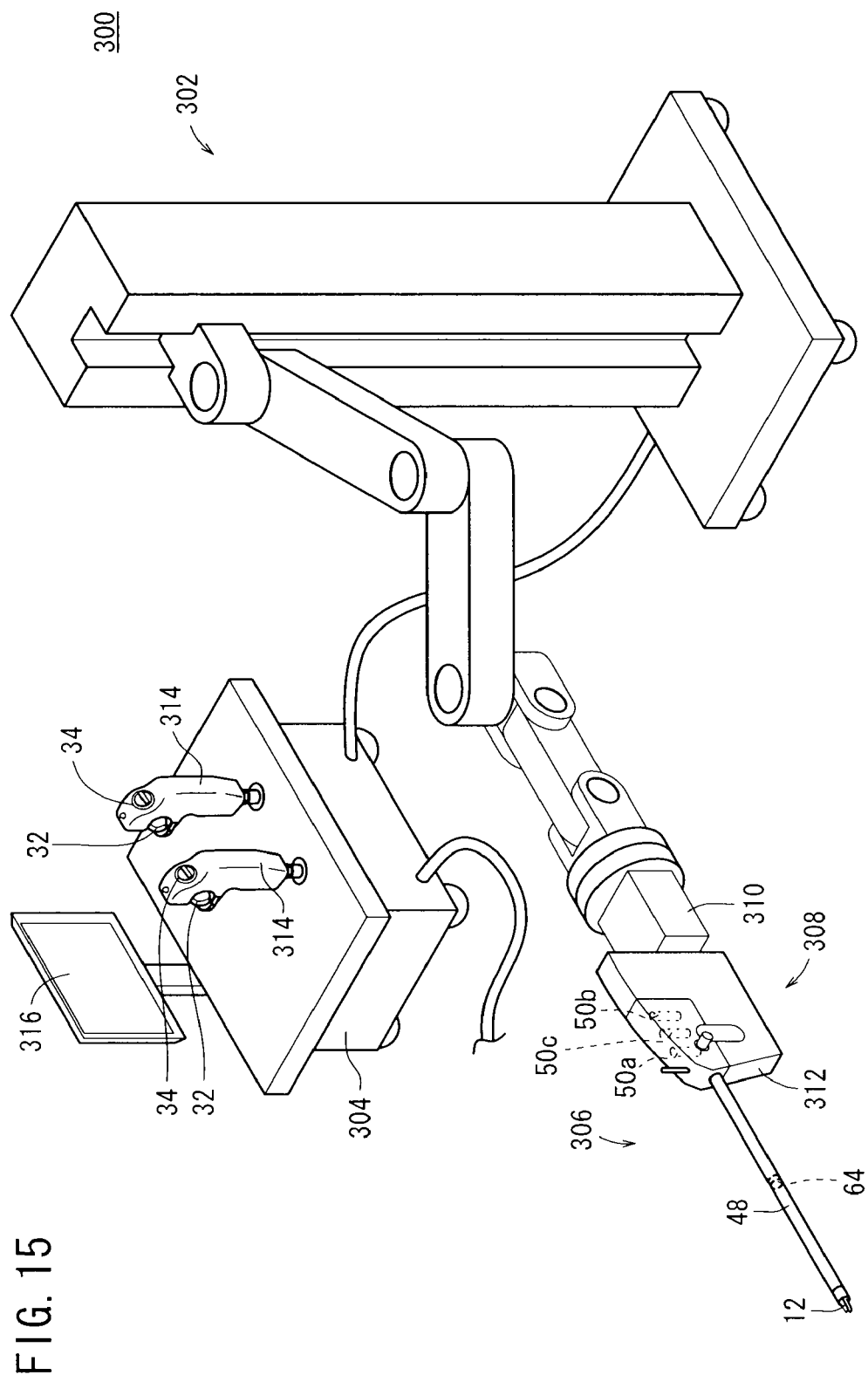
FIG. 15 is a perspective view of a surgical robot system with a working unit connected to the distal end of a robot arm.

The above embodiment may be applied to a surgical robot system 300 shown in FIG. 15, for example.

The surgical robot system 300 has an articulated robot arm 302 and a console 304 with the working unit 306 connected to the distal end of the robot arm 302. The distal end of the robot arm 302 incorporates therein a manipulator 308 having the same mechanism as the manipulator 10. The robot arm 302 may be a means for moving the working unit 306, and is not limited to an installed type, but may be of an autonomous movable type. The console 304 may be of a table type, a control panel type, or the like.

The robot arm 302 should preferably have independent six or more joints (rotary shafts, slide shafts, etc.) for setting the position and orientation of the working unit 306 as desired. The manipulator 308 on the distal end of the robot arm 302 is integrally combined with a distal end 310 of the robot arm 302. The manipulator 308 has, instead of the actuator 30 (see FIG. 1), an actuator block 312 having a proximal end connected to the distal end 310 and housing therein the motors 40a, 40b, 40c (not shown in FIG. 15).

The robot arm 302 is moved under operations of the console 304, and may be automatically actuatable according to a program, or may be actuated by joysticks 314 mounted on the console 304 or by a combination of the program and the joysticks 314. The console 304 includes the function of the controller 45 (see FIG. 1). The working unit 306 includes the distal-end working unit 12.

The console 304 includes the two joysticks 314 as an operation command unit and a monitor 316. Though not shown, the two joysticks 314 are capable of individually operating two robot arms 302. The two joysticks 314 are disposed in respective positions where they can easily be operated by the both hands of the operator. The monitor 316 displays information such as an image produced by an endoscope.

The joysticks 314 can be moved vertically and horizontally, twisted, and tilted, and the robot arm 302 can be moved depending on these movements of the joysticks 314. The joysticks 314 may be in the form of master arms. The robot arm 302 and the console 304 may be connected to each other by a communication means such as a wired link, a wireless link, a network, or a combination thereof.

The sealing member 64 to 64*b* incorporated in the manipulator 308 makes it easy to clean, sterilize, i.e., service the manipulator 308 for maintenance.

Although certain preferred embodiments of the present invention have been shown and described in detail, it should be understood that various changes and modifications may be made therein without departing from the scope of the appended claims.

What is claimed is:

1. A manipulator comprising:
   a hollow shaft;
   a power transmitting member extending through the hollow shaft;
   a drive mechanism mounted on a proximal end of the hollow shaft, the drive mechanism imparting a drive force to the power transmitting member;
   a distal-end working unit mounted on a distal end of the hollow shaft, the distal end working unit being actuated by the power transmitting member;
   a sealing member that prevents liquid from flowing from the distal-end working unit through the hollow shaft to the drive mechanism, the sealing member having a power transmitting member hole defined therein, and the power transmitting member being slidably inserted through the power transmitting member hole; and
   a cleaning tube extending from a drive mechanism side of the manipulator toward a distal-end working unit side of the manipulator, the cleaning tube supplying a cleaning solution therethrough for cleaning an interior of the distal-end working unit;
   wherein the sealing member has a cleaning hole defined therein, the cleaning tube extending through the cleaning hole, and the sealing member being disposed inside the hollow shaft,
   wherein the hollow shaft internally defines a space extending along an axial direction between the distal end of the hollow shaft and the sealing member,
   wherein the cleaning tube has a cleaning solution inlet on a first end at the drive mechanism side, extends through the drive mechanism and the shaft, and penetrates through the sealing member,
   wherein the cleaning tube has a cleaning solution outlet on a second end at the distal-end working unit side, the outlet being disposed, within the space, more closely to the distal-end working unit compared to the sealing member,
   wherein the sealing member has a slit extending from an outer surface thereof to the power transmitting member hole, and
   wherein wall surfaces defining the slit are in close contact with and adhered to each other.

2. A manipulator according to claim 1, wherein the sealing member divides an interior of the hollow shaft into a first compartment near the distal-end working unit and a second compartment near the drive mechanism.

3. A manipulator according to claim 1, wherein the power transmitting member has, at least, a first portion which is flexible and a second portion which is more rigid than the first portion, the second portion extending through the power transmitting member hole.

4. A manipulator according to claim 3, wherein the second portion comprises a reinforcing tube surrounding a portion of the first portion or a bar member coupled to the first portion.

5. A manipulator according to claim 3, wherein when the power transmitting member is operated, the second portion is slidably held in the power transmitting member hole at all times.

6. A manipulator according to claim 1, further comprising a plug removably mounted on the first end of the cleaning tube near the drive mechanism.

7. A manipulator according to claim 1, further comprising a check valve connected to a portion of the cleaning tube which is closer to the drive mechanism than compared to the sealing member, that prevents the cleaning solution from flowing from the distal-end working unit toward the drive mechanism.

8. A manipulator comprising:
   a hollow shaft;
   a power transmitting member extending through the hollow shaft;
   a drive mechanism mounted on a proximal end of the hollow shaft, the drive mechanism imparting a drive force to the power transmitting member;
   a distal-end working unit mounted on a distal end of the hollow shaft, the distal end working unit being actuated by the power transmitting member;
   a sealing member that prevents liquid from flowing from the distal-end working unit through the hollow shaft to the drive mechanism, the sealing member having a power transmitting member hole defined therein, the power transmitting member being inserted through the power transmitting member hole, and an elastic member disposed in the power transmitting member hole and fixedly mounted on an outer circumferential surface of the power transmitting member; and
   a cleaning tube extending from a drive mechanism side of the manipulator toward a distal-end working unit side of the manipulator, the cleaning tube supplying a cleaning solution therethrough for cleaning an interior of the distal-end working unit;
   wherein the sealing member has a cleaning hole defined therein, the cleaning tube extending through the cleaning hole, and the sealing member being disposed inside the hollow shaft,
   wherein the hollow shaft internally defines a space extending along an axial direction between the distal end of the hollow shaft and the sealing member,
   wherein the cleaning tube has a cleaning solution inlet on a first end at the drive mechanism side, extends through the drive mechanism and the shaft, and penetrates through the sealing member,
   wherein the cleaning tube has a cleaning solution outlet on a second end at the distal-end working unit side, the outlet being disposed, within the space, more closely to the distal- end working unit compared to the sealing member,
   wherein the sealing member has a slit extending from an outer surface thereof to the power transmitting member hole, and
   wherein wall surfaces defining the slit are in close contact with and adhered to each other.

9. The manipulator according to claim 1, wherein a ring is disposed against the sealing member inside the hollow shaft, thereby securing the sealing member in position.

10. The manipulator according to claim 1, wherein the hollow shaft includes an annular ridge that abuts the sealing member.

11. The manipulator according to claim 4, wherein the reinforcing tube is crimped around the power transmitting member on each end thereof.

12. The manipulator according to claim 9, wherein the ring is bonded or welded to an inner circumferential surface of the hollow shaft.

13. The manipulator according to claim 9, wherein the ring is press-fitted in the hollow shaft.

14. The manipulator according to claim 1, wherein the cleaning hole and the power transmitting member hole of the sealing member are separate and distinct.

\* \* \* \* \*